United States Patent [19]
Lewin

[11] Patent Number: 6,035,698
[45] Date of Patent: Mar. 14, 2000

[54] APPARATUS FOR TESTING HUMIDITY OF GAS STREAM

[76] Inventor: Henry Lewin, 9025 Fox Lair Dr., Burke, Va. 22015

[21] Appl. No.: 09/052,171

[22] Filed: Mar. 31, 1998

Related U.S. Application Data

[60] Provisional application No. 60/042,455, Mar. 31, 1997.

[51] Int. Cl.[7] .................................................. G01N 33/00
[52] U.S. Cl. ........................................ 73/29.01; 340/453
[58] Field of Search .............................. 73/29.01, 29.02, 73/863.8, 866.5, 23.2; 340/453

[56] References Cited

U.S. PATENT DOCUMENTS

| | | |
|---|---|---|
| 4,949,744 | 8/1990 | Heed et al. .............................. 137/15 |
| 4,999,035 | 3/1991 | Warndorf .................................. 55/275 |
| 5,257,008 | 10/1993 | Elamin .................................... 340/540 |
| 5,343,735 | 9/1994 | Succi et al. ........................... 73/29.01 |
| 5,377,532 | 1/1995 | Urza ........................................... 73/73 |
| 5,452,621 | 9/1995 | Aylesworth et al. ................ 73/864.81 |

*Primary Examiner*—Michael Brock
*Attorney, Agent, or Firm*—Evenson, McKeown, Edwards & Lenahan, P.L.L.C.

[57] ABSTRACT

An apparatus for measuring the dew point humidity of air, e.g. from compressed air lines of any tupe (for example, brake lines of railroad trains), composed of a conduit with a connector at one end for connecting the conduit to a source of air to be measured, a T-branch in which a probe of a dew point humidity meter is receive with the tip of the probe extending into a stream of air or other gas flowing through the conduit, and an electrical power supply for the meter, all arranged in a convenient, portable assembly.

5 Claims, 1 Drawing Sheet

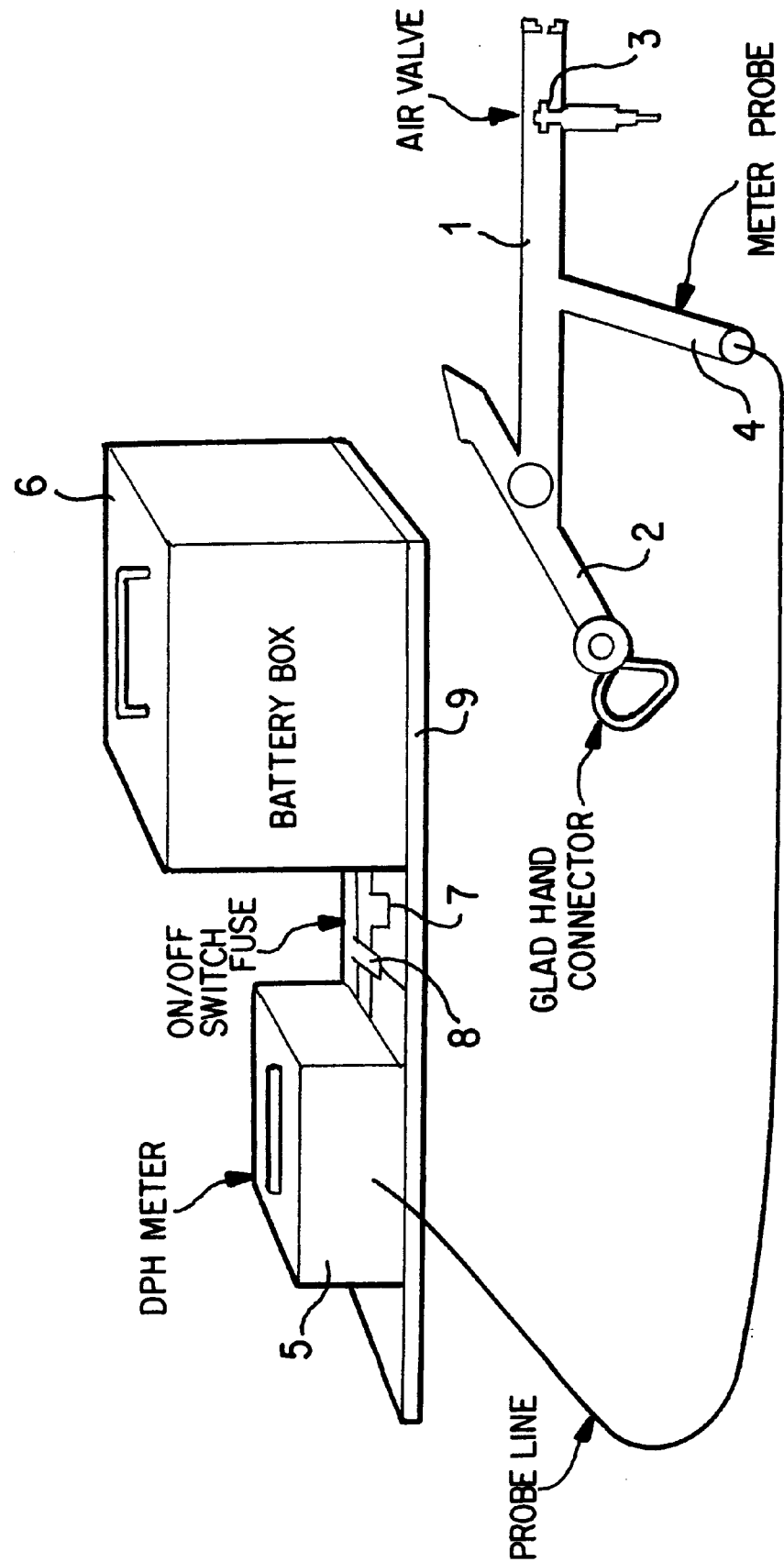

APPARATUS FOR TESTING HUMIDITY OF GAS STREAM

This application claims the benefit of US. Provisional No. 60/042,455 filed Mar. 31, 1997.

SUMMARY OF THE INVENTION

The present invention relates to an improved apparatus for testing of air humidity from compressors or other sources of flow, movement or compression using a Dew Point Depression Humidity Device (DPH).

Specifically, the invention allows the user of a DPH device to easily attach and detach the DPH and similar type devices to and from numerous sources of air to be tested, e.g., from locomotive to locomotive, to train line of a train, to a yard compressor, to a plant line, etc.

The invention comprises an adaptor for existing DPH devices which makes the DPH portable by providing an electrical supply (battery, or air powered generator) to run the DPH device whether or not a direct power supply exists.

Features and advantages of the invention include the following:

1. A DPH device with an electrical supply in the form of a battery. (An internal air powered generator could be utilized to generate electrical power to run the DPH meter).
2. A fuse which protects the DPH device from surge and a switch for interrupting the flow of current to the DPH device. (A circuit breaker could also be utilized in place of the fuse.)
3. A backboard on which the DPH device, the wire, switch, circuitry and battery are mounted. (A plate could be used instead of a back board.)
4. A "T" piping configuration which the DPH device probe is inserted into, exposes the tip of the probe to the cross section of the T arrangement. While the probe could be inserted into a configuration in any number of ways or angles that would allow air flow to pass over the probe, the above description provides adequate air flow to obtain optimal readings. A valve suitable to open and close the flow of air is at one end of the T arrangement. While the valve is not necessary, it is a safe and convenient means to regulate the air flow.
5. At the other end of the T adapter is an attachment which allows the device to be connected to the output source from the compressor. A variety of attachment adapters may be utilized. In the attached FIGURE a Glad Hand assembly is utilized to attach directly to the end of the train line air hose, which is the standard in the railroad industry on locomotive cars and yard compressed air plant line supply.
6. This device allows the user to go from locomotive to locomotive to yard compressor to plant line with relative ease and without the need to modify or redesign existing equipment to enable the moisture content of the air or other gas to be read using the DPH device. The drilling and tapping of a hole in the air reservoir is avoided by using the adapter thus saving thousands of man hours in modifying equipment and installing the probe in each piece of equipment.

The valve utilized at the end of the T arrangement may be used to regulate the rate of flow of the air, usually expressed in cubic feet per minute (CFM). A typical DPH device requires an air flow of approximately 60 CFM or more to provide an accurate reading. A choke or orifice designed with a predetermined diameter for a predetermined air pressure may also be used, however, such predetermined airflow may not necessarily be desirable when testing varying air compressors whose output varies from a wide variety of pressures (PSI).

BRIEF DESCRIPTION OF THE DRAWING

The invention will be described in further detail hereinafter with reference to an illustrative preferred embodiment shown in the attached FIGURE, which is a schematic representation of an embodiment of the invention.

DETAILED DESCRIPTION OF A PREFERRED EMBODIMENT

The attached drawing shows a conduit 1 through which a flow of air or other gas to be tested may be established. Conduit 1 may be made of any suitable material such as metal or plastic. Conduit 1 has a conventional glad hand connector 2 at one end which enables the conduit to be connected to a railroad locomotive air line in order to measure the dew point humidity of the compressed air therein. Of course, other types of connectors could be used for connection to other types of systems. A valve 3 is also provided on the conduit to regulate the flow of air or other gas through the conduit.

A branch tube 4 tees off from conduit 1. Branch tube 4 is adapted to receive a probe of a dew point humidity meter 5, with the tip of the probe extending into a stream of air or other gas to be tested flowing through conduit 1. Suitable dew point depression humidity testers are known in the art. For example, one suitable dew point depression humidity test device for use in the present invention is commercially available from Vaisala Inc., 100 Commerce Way, Woburn, Mass. 01801, Model HMP 234. The meter 5 can measure and indicate and/or record parameters such as relative humidity, absolute humidity, dew point, mixing ratio, temperature, and/or wet bulb temperature.

Dew point meter 5 is powered by a battery 6, which is operatively connected to the meter 5 through a fuse 7 and a switch 8. Alternatively, other types of power sources could be used, such as a turbine driven generator powered by the gas stream being tested. In the illustrated embodiment, dew point meter 5, battery 6, fuse 7 and switch 8 are all mounted on a common support plate 9, for convenient portability. Of course, other types of mounting arrangements could be used, for example, a wheeled housing.

The foregoing description and examples have been set forth merely to illustrate the invention and are not intended to be limiting. Since modifications of the disclosed embodiments incorporating the spirit and substance of the invention may occur to persons skilled in The art, the invention should be construed to include everything within the scope of the appended claims and equivalents thereof.

What is claimed is:

1. An apparatus for testing humidity of a gas comprising:

a conduit for a stream of gas to be tested;

a glad hand connector for connecting said conduit to a railroad train air brake air line at one end of said conduit for connecting said conduit to a source of gas to be tested;

a branch tube on said conduit;

a dew point depression humidity tester having a probe; said probe being received in said conduit branch tube such that the probe extends into a stream of gas flowing through said conduit; and an electrical power source for said dew point depression humidity tester.

2. An apparatus according to claim 1, wherein said conduit and conduit branch tube form a tee connection.

3. An apparatus according to claim 1, wherein said power source comprises an electrical battery connected to the dew point depression humidity tester through a switch.

4. An apparatus according to claim 3, further comprising a fuse or circuit breaker interposed between the battery and the dew point depression humidity tester.

5. An apparatus according to claim 1, further comprising a valve on said conduit for regulating gas flow through the conduit.

* * * * *